United States Patent
Doutre

[11] Patent Number: 5,834,928
[45] Date of Patent: Nov. 10, 1998

[54] METHOD AND APPARATUS FOR THE DETECTION AND MEASUREMENT OF SOLID PARTICLES IN MOLTEN METAL

[75] Inventor: Don Allen Doutre, Kingston, Canada

[73] Assignee: Alcan International Limited, Montreal, Canada

[21] Appl. No.: 725,001

[22] Filed: Oct. 1, 1996

Related U.S. Application Data

[60] Provisional application No. 60/004,761, Oct. 4, 1995.

[51] Int. Cl.[6] .................................................. G01N 27/02
[52] U.S. Cl. ........................... 324/71.4; 164/4.1; 266/99; 324/71.1
[58] Field of Search ................................ 324/71.4, 71.1, 324/724, 715, 717; 266/99; 164/4.1

[56] References Cited

U.S. PATENT DOCUMENTS

| | | | |
|---|---|---|---|
| 3,924,180 | 12/1975 | Salzman et al. | 324/71.4 |
| 4,019,134 | 4/1977 | Hogg | 324/71.4 |
| 4,434,398 | 2/1984 | Berg et al. | 324/71.4 |
| 4,555,662 | 11/1985 | Doutre et al. | 324/71.4 |
| 4,600,880 | 7/1986 | Doutre et al. | 324/71.4 |
| 4,763,065 | 8/1988 | Hachey | 324/71.4 |
| 4,926,114 | 5/1990 | Doutre | 324/71.4 |
| 5,039,935 | 8/1991 | Hachey et al. | 324/71.4 |
| 5,130,639 | 7/1992 | Hachey | 324/71.4 |
| 5,198,749 | 3/1993 | Guthrie et al. | 324/71.4 |
| 5,241,262 | 8/1993 | Guthrie et al. | 324/71.4 |
| 5,489,506 | 2/1996 | Crane | 324/71.4 |
| 5,500,992 | 3/1996 | Barnes et al. | 324/71.4 |

Primary Examiner—Maura K. Regan
Attorney, Agent, or Firm—Cooper & Dunham LLP

[57] ABSTRACT

A method and apparatus for detecting and measuring suspended solid particles in a molten metal, even if the metal also contains liquid and/or gaseous inclusions. The method involves moving molten metal through an orifice of predetermined hydrodynamic diameter provided in an electrically non-conductive barrier. As the molten metal is moved through the orifice, a current path is established by passing a current through the orifice from electrodes positioned on opposite sides of the barrier. Changes in voltage of the current are measured as the metal is drawn through the orifice, and the number of particles suspended in said metal drawn through the orifice is detected from the voltage changes. The metal, immediately before being moved through the orifice, is conveyed through a passage defined by an electrically non-conductive surface positioned in the current path, the passage including a region having a hydrodynamic diameter of between 2 and 10 times the hydrodynamic diameter of the orifice, at least a part of the region being of substantially constant hydrodynamic diameter. The provision of the passage upstream of the orifice has the effect of removing substantially all liquid and gaseous inclusions from the molten metal before the metal passes through the orifice.

52 Claims, 4 Drawing Sheets

METHOD AND APPARATUS FOR THE DETECTION AND MEASUREMENT OF SOLID PARTICLES IN MOLTEN METAL

CROSS REFERENCE TO RELATED APPLICATION

This application is a continuation of U.S. provisional application Ser. No. 60/004,761 filed Oct. 4, 1995.

BACKGROUND OF THE INVENTION

1. Field of the Invention

The present invention relates to a method and apparatus for the detection and measurement of inclusions in molten metal. More particularly, the invention relates to the detection and measurement of solid particles in such metal.

2. Description of the Prior Art

Molten metals, particularly molten aluminum and steel, are frequently contaminated to some extent by non-metallic inclusions that give rise to defects in the final products. These inclusions can be solids, such as refractory particles including oxides of the metal in question, liquids, such as molten salts from various fluxing operations, or gases, such as gas bubbles retained in the molten metal as a result of metal degassing operations.

An apparatus and method for the measurement of inclusions in molten metals is described in U.S. Pat. No. 4,555,662 issued to Doutre et al. on Nov. 26, 1985 and assigned to Limca Research Inc. The method is based on establishing a current flow between two electrodes immersed in the molten metal on opposite sides of an orifice in an electrically non-conductive barrier, passing the molten metal containing inclusions through the orifice, and measuring voltage pulses caused by inclusions as they pass through the orifice. The size of the voltage pulses, and hence the ability of the apparatus to measure inclusions, is dependent on the metal, the size of the inclusions, the orifice size and the size of the current flow. For metals such as aluminum, substantial currents are required. Orifice sizes (diameters or cross-sectional areas) are relatively small, being only 10 to 20 times the size of the particles to be measured. The length of the orifice is also selected to ensure that only one particle is effectively within the orifice at a time. The shape of the orifice is also found to be important in achieving good signals and reliable operation. For example, a smooth edged orifice, with edges, viewed in cross-section, of semi-circular shape are suitable. Such an orifice is shown, for example, in FIG. 4 of U.S. Pat. No. 4,555,662.

The apparatus disclosed by Doutre et al. detects and measures inclusions having electrical conductivities different from that of the molten metal in which they are suspended, and therefore does not normally differentiate between solid, liquid and gaseous inclusions. However, it is generally desirable to determine the number of solid particles in the molten metal independently of the liquid or gaseous inclusions, as the solid particles are of most concern for product quality. This is not possible by measurement of the voltage pulses in the apparatus described above. Furthermore, where there are large numbers of gaseous or liquid inclusions present (for example, downstream of an in-line metal degassing or fluxing process), the number of such non-solid inclusions may greatly exceed the number of solid inclusions, and in some instances can cause instability of the flow in the orifice, which hinders the use of the apparatus and method in measuring the solid inclusions of interest.

SUMMARY OF THE INVENTION

An object of the present invention is accordingly to provide a method and apparatus for the detection and measurement of concentrations of solid particulates in molten metals.

Another object of the invention is to provide a method and apparatus for the detection and measurement of concentrations of solid particulates in molten metals in the presence of liquid and/or gaseous inclusions.

According to one aspect of the invention, there is provided a method of detecting and measuring solid particles suspended in a molten metal. The method involves moving molten metal through an orifice of predetermined hydrodynamic diameter provided in an electrically non-conductive barrier, and, as the molten metal is moved through the orifice, establishing a current path passing through the orifice from electrodes positioned on opposite sides of the barrier. Changes in voltage of the current are detected as the metal is moved through the orifice, and the presence and size of particles suspended in the metal moved through the orifice are detected from the voltage changes. In order to eliminate non-solid particles from the metal passing through the orifice, the metal, immediately before being passed through the orifice, is moved through a passage including a region having a hydrodynamic diameter of between 2 and 10 times the hydrodynamic diameter of the orifice, at least a part of the region being of substantially constant hydrodynamic diameter.

According to another aspect of the invention, there is provided apparatus for detecting and measuring suspended solid particles in a molten metal. The apparatus includes an electrically non-conductive barrier having opposed sides and having an orifice of predetermined hydrodynamic diameter, the barrier being suitable for immersion in a molten metal with the orifice below a surface of the metal. The apparatus includes a device for moving molten metal through the orifice in a direction from one side of the barrier to the other, and electrodes, suitable for immersion in the metal, positioned on opposite sides of the barrier for establishing a current path in the metal passing through the orifice. A current generator is provided for connection to the electrodes when the barrier and the electrodes are immersed in the metal and a voltage detecting device is provided for detecting changes in voltage as current flows through the metal between the electrodes as the metal moves through the orifice. Processing apparatus detects and determines the number of particles in the molten metal passing through the orifice from the changes in voltage. The apparatus includes an electrically non-conductive surface adjacent to an upstream side of the orifice, considered in the direction of movement of the metal through the orifice, defining a passage for conveying molten metal to the orifice, the passage including a region having a hydrodynamic diameter of between 2 and 10 times the hydrodynamic diameter of the orifice, at least a part of the region being of substantially constant hydrodynamic diameter.

According to yet another aspect of the invention, there is provided a probe for use in apparatus for detecting and measuring suspended solid particles in a molten metal. The probe includes an electrically non-conductive barrier resistant to damage by molten metal and provided with an orifice of predetermined hydrodynamic diameter, and an electrically non-conductive surface adjacent to an upstream side of the orifice, considered in the direction of movement of the metal through the orifice, defining a passage for conveying molten metal to the orifice, the passage including a region having a hydrodynamic diameter of between 2 and 10 times the hydrodynamic diameter of the orifice, at least a part of the region being of substantially constant hydrodynamic diameter.

The term "hydrodynamic diameter" as used in this specification is defined, for example, in Perry's Chemical Engineering Handbook, 5th Edition, Page 5-4, Table 5–11, as four times the hydraulic radius, which in turn is equal to the cross-sectional area of the passage (or orifice) divided by the perimeter of the passage (or orifice). For cylindrical passages, the hydrodynamic diameter is equal to the actual diameter.

The region of the passage where the hydrodynamic diameter is between 2 and 10 times the hydrodynamic diameter of the orifice has a length in the longitudinal direction of the passage that is preferably at least equal to the hydrodynamic diameter of the passage (in the part of substantially constant cross section) and, more preferably, the ratio of this length to the square of the hydrodynamic diameter of the passage (in the part of substantially constant cross section) is at least 1000 meters$^{-1}$. At least a part of this region of the passage is preferably of substantially constant diameter. For ease of manufacture, at least a majority, and more preferably all, of the region is of substantially constant hydrodynamic diameter.

The passage is preferably defined (delimited and circumscribed) by an internal surface of an open-ended hollow, preferably tubular, projection extending outwardly from the barrier on the upstream side considering the direction of movement of the metal through the orifice during the measuring step. The tubular projection may be attached to or form part of the barrier, and is made of (or coated at least internally with) an electrically non-conductive material that may be the same as the material of the barrier or different, and that surrounds the orifice at the end connecting to the barrier. The projection extends for a suitable length away from the barrier and thus defines a passage that is positioned in the current path and that directs the metal to the orifice during the measuring step.

Alternatively, the passage may be defined by an internal surface of the barrier itself, rather than a projection from the barrier, if the barrier is sufficiently thick in the region of the orifice (e.g. at least about three times the wall thickness of 1 to 1.5 mm employed in some conventional devices). In such a case, a hole would penetrate completely through the barrier from one side to the other. At or adjacent to one side of the barrier, the hole would be relatively small and would thus define the orifice required for testing. Continuing in a direction towards the opposite side of the barrier, the through hole would increase in diameter, and the internal surface of the hole in this region would form the required passage upstream of the orifice.

In either case, the barrier is preferably the wall of a closed hollow test vessel forming part of a probe to be immersed into the molten metal, and the device for moving the metal through the orifice is preferably a vacuum source (e.g. a vacuum pump connected to a pressure tank that can be evacuated) connectable to the interior of the test vessel or probe.

Since the method relies on differences in electrical conductivity caused by solid particles as they pass through the orifice, the method is of course only effective for detecting and measuring particles that have an electrical conductivity different from that of the surrounding molten metal.

Generally, orifice diameters from 100 to 5000 micrometers, and more usually 200 to 500 micrometers, are usable in this invention, although diameters outside this range may be suitable for special applications. The orifice diameter is selected based on the particle size range to be measured. The orifice dimension (hydrodynamic diameter) is assumed to be the minimum opening dimension in those cases where the orifice is not of constant hydrodynamic diameter throughout its length, e.g. in the case where the orifice walls are in the preferred smooth-edged form mentioned above. Although there is no critical relationship between the particle size and orifice size, it can generally be stated that, for an orifice of a given size, the lower limit of measurable particle size is determined by the detectablility of the particle signal over background noise, whereas the upper limit is determined by the probability of blocking the orifice if too many such particles are present. For example, in aluminum, with inclusions in the 20 to 80 micrometer range, an orifice diameter of 300 micrometers is suitable. Inclusions in steel are often larger and a larger diameter orifice may be selected.

The passage adjacent to the orifice is preferably of circular cross section but may be of any other shape, and in one embodiment has a constant cross-sectional area throughout its length. Alternatively, the passage may have a first outermost part (remote from the orifice) of constant cross-section and a second innermost part (adjacent to the orifice) of smaller cross-section, the extreme inner end of which may form the orifice itself. Most preferably, the cross-sectional area or hydrodynamic diameter of the second part gradually reduces in size along its length in the direction approaching the orifice.

In any form of the invention, the means for detecting voltage or voltage changes may be connected to the current electrodes or connected to one or more additional electrodes provided for this purpose, as will be apparent from the following description.

DETAILED DESCRIPTION OF THE INVENTION AND THE PREFERRED EMBODIMENTS

The present invention can be operated as a modification of known metal inclusion measurement apparatus, e.g. as described in U.S. Pat. No. 4,555,662 mentioned above, U.S. Pat. No. 5,039,935 issued on Aug. 13, 1995 to Hachey et al. and assigned to Alcan International Limited, and U.S. Pat. No. 5,130,639 issued on Jul. 14, 1992 to Hachey and assigned to Alcan International Limited, the disclosures of all of which are incorporated herein by reference. When the metal to be tested is aluminum, the invention is particularly preferred when used in the type of apparatus shown in FIG. 8 of U.S. Pat. No. 5,130,639. Such an apparatus is available commercially as the Limca II particle analyser, manufactured by Bomem, a subsidiary of Hartmann-Braun of Quebec, Canada.

Essentially, the device used for moving molten metal through an orifice used for detecting inclusions, and the circuitry and apparatus used for the measurement and interpretation of voltage pulses in the current flowing through the orifice, may be basically the same in the present invention as in the known prior art apparatus. The present invention differs from the known apparatus, inter alia, in the way in which the molten metal is treated immediately before it flows through the detection orifice, and in the apparatus used to effect such pretreatment, as will be apparent from the following description.

Figure 1:
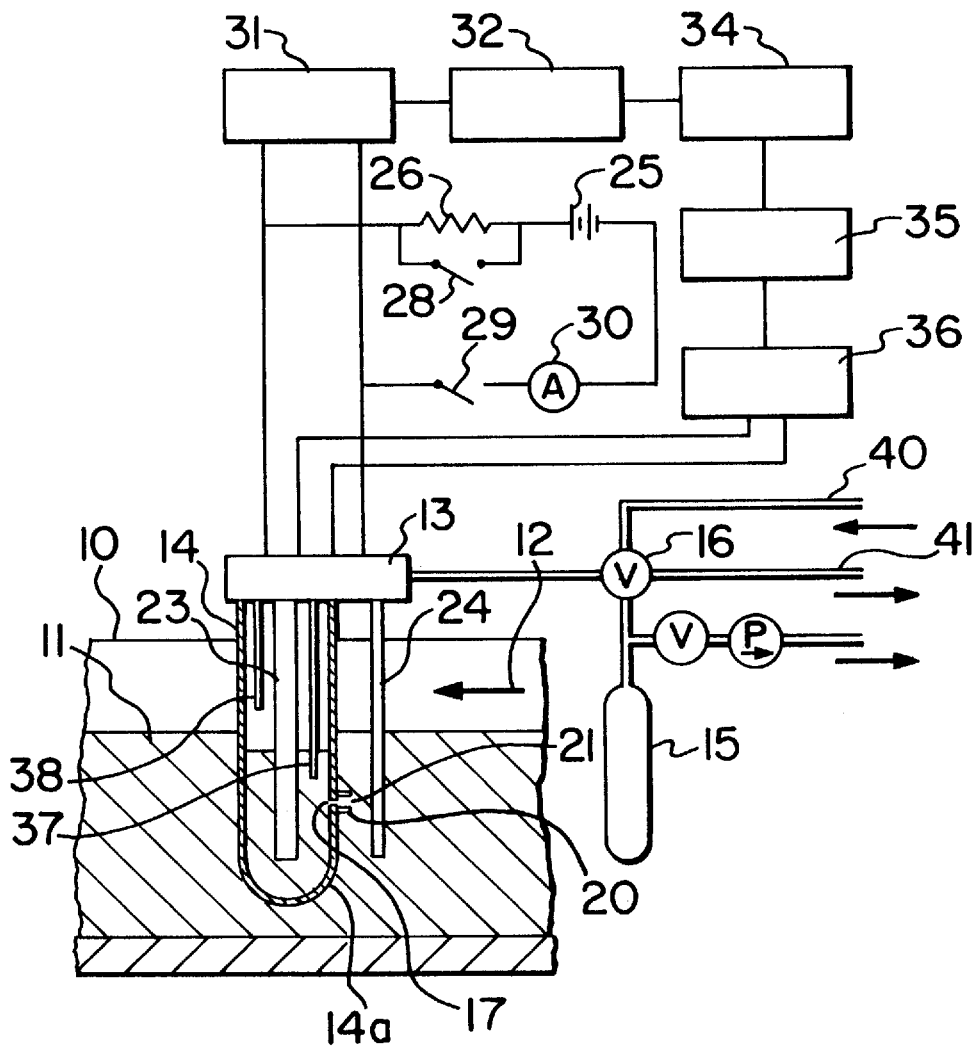
FIG. 1 a simplified schematic view showing an operative arrangement for measuring metal inclusions embodying a preferred form of the present invention.

FIG. 1 is a simplified view of a preferred form of the apparatus and circuitry employed in the present invention. A metal delivery trough 10 conveys molten metal 11, to be tested for solid inclusions, in the direction of arrow 12. The apparatus includes a closed test vessel 14 having an outer wall 14a, forming a barrier to molten metal flow, made of an electrically non-conductive material firmly held in a retaining head 13 supplied with a source of vacuum 15 via a valve 16. To carry out a test procedure, the test vessel is lowered into the molten metal, the vacuum source is connected to the interior of the test vessel and, as shown more clearly in FIG. 2, metal 11 is drawn into the vessel through an orifice 17 after first passing through a short cylindrical projection 20 defining a passage 21.

The retaining head 13 holds two downwardly-extending electrodes 23 and 24, one positioned inside the vessel 14 and the other positioned outside, but adjacent to, the test vessel facing the projection 20. The electrodes are connected to a source of DC current, such as battery 25, via a ballast resistor 26 that can be shunted when required by a switch 28, one of the electrical leads including a switch 29 and an ammeter 30. Although not shown, the electrodes 23 and 24 may be covered by layers of electrically insulating material except adjacent to their lower ends in the region of the orifice 17. The resultant current path formed in the molten metal between the electrodes 23 and 24 flows through the orifice 17 and the passage 21 inside the tubular projection 20.

The electrodes 23, 24 are connected to a differential amplifier 31 and then to a logarithmic amplifier 32, a peak detector 34 and a multichannel analyser 35, which can also serve as a recorder. The analyser/recorder 35 is operated automatically so as to be switched on when sufficient metal has entered the test vessel 14 to contact a lower level electrode 37 of a metal level detector 36, and to be switched off when sufficient metal has entered to contact an upper level electrode 38 of the level detector. Alternatively, the analyser/recorder can be operated manually, the sampling period used then being a fixed period of time as set by the operator.

Before use, the interior of the test vessel 14 is flushed with argon gas from line 40 by suitably positioning valve 16 to avoid contamination of the metal by air. The valve 16 can also connect the vessel to atmosphere via line 41 for venting, when desired.

After flushing, the vessel 14 is lowered into the molten metal and connected to the source of vacuum 15, whereupon molten metal is drawn smoothly and rapidly through the tubular projection 20 and the orifice 17 into the interior of the vessel. As soon as enough metal has entered the vessel to touch the lower tip of electrode 23, a current path is established between the two electrodes 23, 24 and through the passage 21 and the orifice 17.

The current flow is principally controlled by the ballast resistor 26 and this remains sufficiently constant (less than 1% variation) during signal processing. Since the area of contact between the liquid metal 11 and the electrodes 23, 24 is preferably limited to the lower parts of the electrodes, the only changes in voltage that are measured are those arising from the displacement of conducting fluid by particles passing through the orifice 17. Each of these particles, when sensed, produces a record consisting of a voltage pulse over and above the steady state value. As is known, these pulses can be used to measure the concentration and sizes of the particles in the metal.

The present invention is remarkable in that the apparatus measures only solid particles in the metal and ignores liquid and gaseous inclusions. This is because liquid and gaseous particles, if present, are substantially completely removed from the metal before the metal passes through the orifice 17, and therefore the voltage pulses measured are those due to solid particles only. This is achieved by means of the short cylindrical projection 20 provided around the orifice 17 defining a passage 21 in the current path that extends between the electrodes 23, 24 through the orifice 17, as will be described in more detail with reference to FIG. 2.

The cylindrical projection 20 may be made from the same material as the test vessel 14 or a different material, provided that the cylindrical projection can be joined effectively to the vessel. The vessel 14 may itself be manufactured in a variety of materials dependent on the metal to be used. For example, when testing aluminum, borosilicate glass or aluminosilicate glass may be used. In this case, the cylindrical projection may be conveniently attached to the test vessel by glass blowing techniques, and the orifice may be formed by flame piercing as disclosed in U.S. Pat. No. 4,555,662, the disclosure of which is incorporated herein by reference. The cylindrical projection has an internal passage 21 of constant diameter 42 over a length 43, except at the point of attachment to the vessel, where a smooth transition 22 occurs as a result of the glass blowing technique. When testing steel, alumina may be used as the material of the test vessel and projection. The cylindrical projection 20 and the vessel may in some cases be formed as a single piece, with the small orifice 17 formed in a separate (drilling or boring) operation.

The inner diameter 42 of the cylindrical projection 20 must be at least twice the diameter of the orifice 17 and less than 10 times the diameter of the orifice 17. The length 43 of the projection (and thus the passage it defines) is at least equal to the diameter 42 (hydraulic diameter). The ratio of the length 43 of the projection to the square of the diameter 42 (or hydraulic diameter) of the tube 20 should preferably be at least 1000 meters$^{-1}$. Accordingly, in this embodiment, the region of the passage having the required ratio of hydrodynamic diameter to the hydrodynamic diameter of the orifice, and the part of this region of substantially constant cross section, are essentially the same, namely substantially the entire length of the passage.

Figure 3:
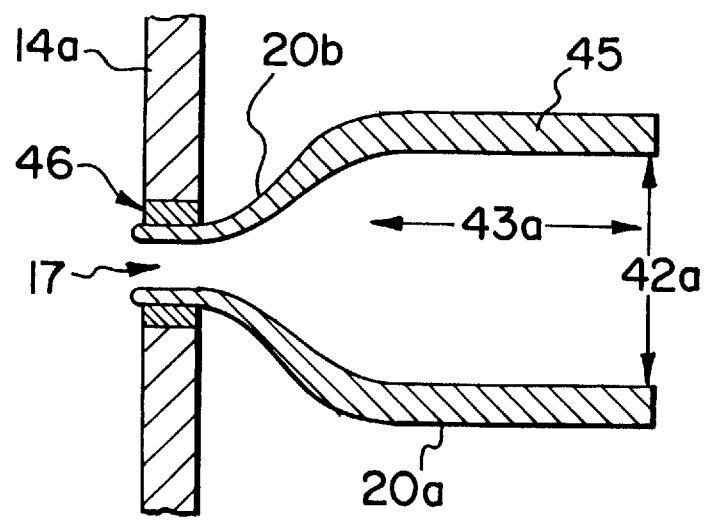
FIG. 3 is an enlarged cross-section similar to FIG. 2 showing a second embodiment of an orifice and passage.

An orifice 17 and projection 20 of a second embodiment of the invention are shown in FIG. 3. In this case, the orifice and projection are formed as a single piece 45 from non-conductive material. The projection 20 consists of an outermost part 20a of substantially constant cross-sectional area having a length 43a that is at least as great as its diameter 42a (or the hydrodynamic diameter when the passage is of non-circular cross section). More preferably, the ratio of the length 43a to the square of the diameter 42a (or hydrodynamic diameter) is at least 1000 m$^{-1}$. The orifice 17 is formed at the end of the piece of material 45 by reducing the size to a diameter suitable for measuring the desired particles, as described elsewhere in this disclosure. An intermediate part 20b may be provided, which does not affect the operation substantially if made suitably short. This can be achieved for example if the length of the intermediate part 20b does not exceed the diameter (or hydrodynamic diameter) of the part 20a. If the length of the intermediate part 20b is substantially greater than the diameter of the part 20a, the narrow end of the part 20b can effectively form part of the orifice 17 and contribute to the change in voltage caused by the particles passing through the orifice. This results in changes to the observed voltage pulses and affects the ability of the apparatus to measure particles. Accordingly, in this embodiment, the region having the required ratio of hydrodynamic diameter is essentially the same as the part of the region of substantially constant hydrodynamic diameter, namely the part 20a.

The single piece 45 is mounted in the wall 14a of the vessel (as shown in FIG. 1) acting as a barrier for the molten metal. The single piece 45 may be made from a material different from that of the wall 14a provided the materials are compatible and can be joined to each other, possibly using transition materials 46. Suitable combinations are generally known, for example, in the field of glass blowing, as are methods of joining. The diameter 42a (hydrodynamic diameter) is between 2 and 10 times the diameter of the orifice 17, as in other embodiments.

Figure 2:
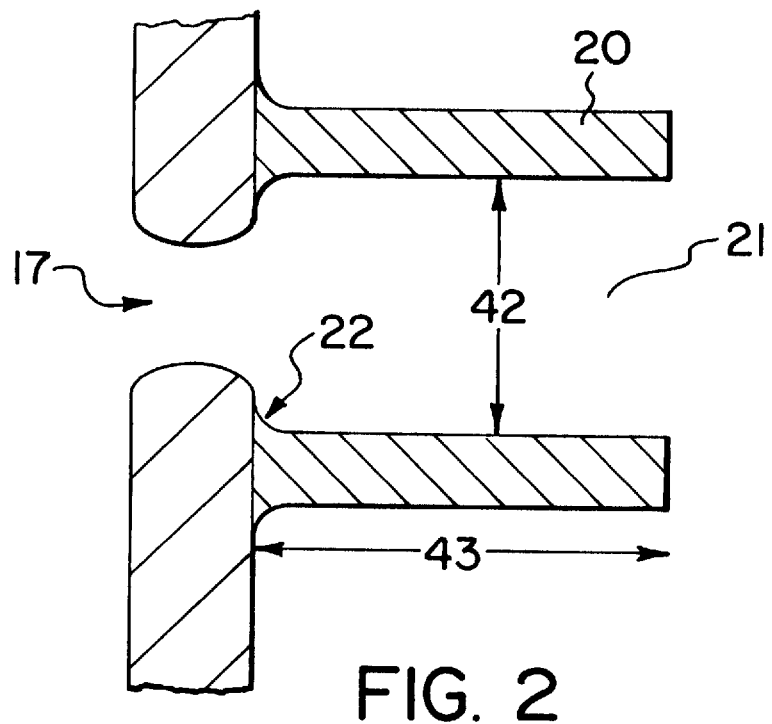
FIG. 2 is simplified cross-sectional view, on an enlarged scale, of part of the apparatus of FIG. 1, showing a preferred form of an orifice and passage as required by the present invention.
Figure 4:
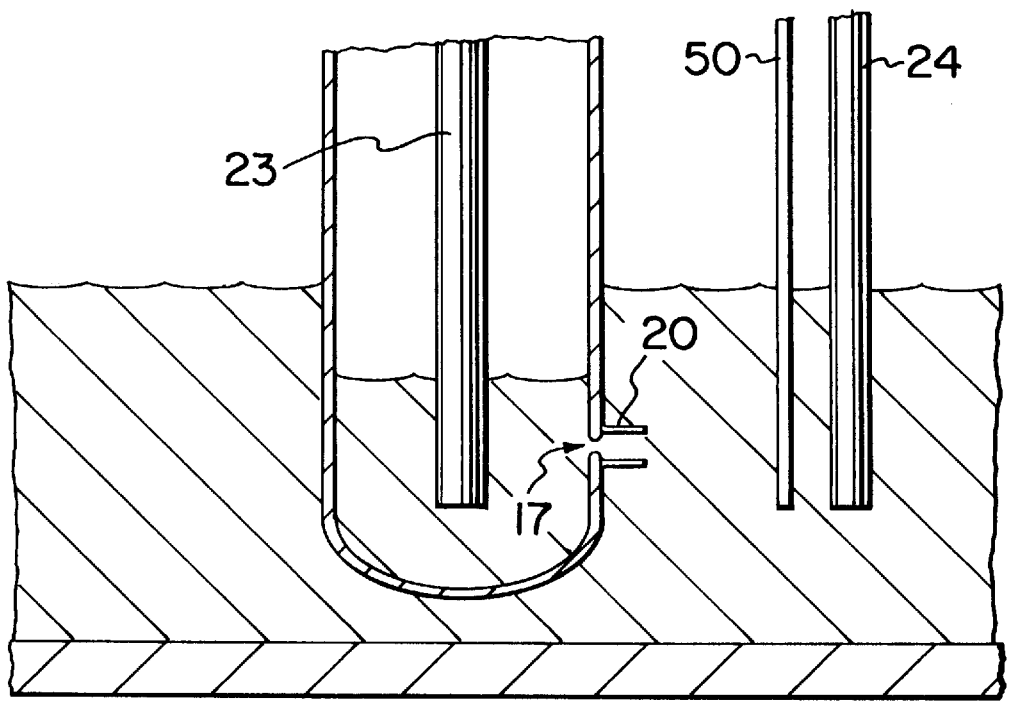
FIGS. 4, 5 and 6 are views somewhat similar to FIG. 1, but showing just the different parts of alternative embodiments of the present invention.
Figure 5:
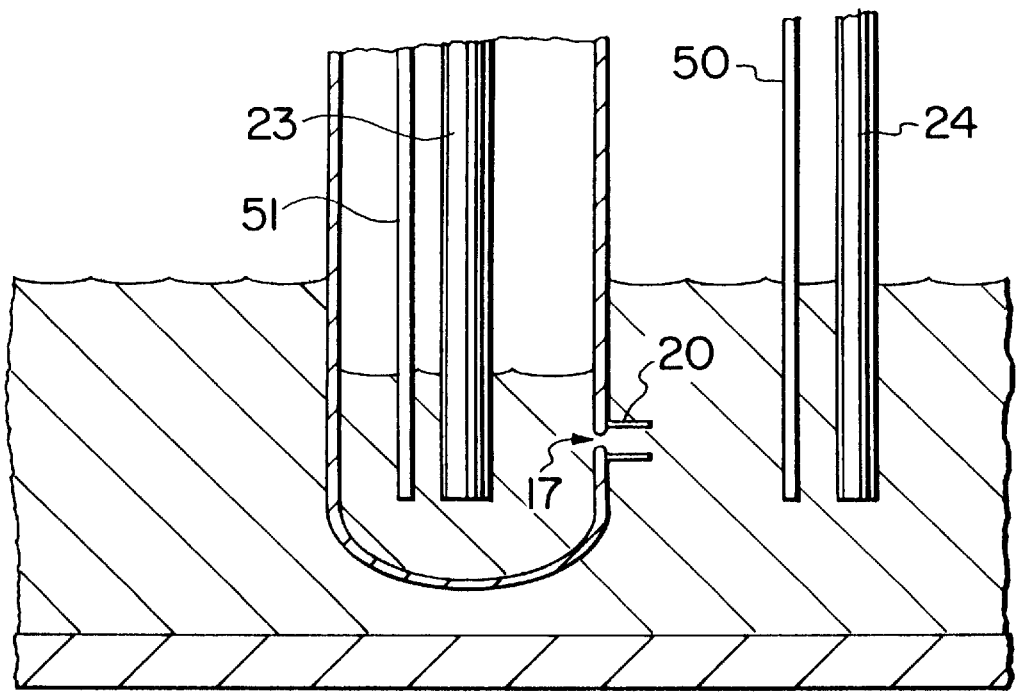

FIGS. 4 and 5 show details of apparatus similar to that of FIGS. 1 and 2 except for the number of electrodes which are present. FIG. 4 shows a three-electrode apparatus. In addition to the electrodes 23, 24 used for the supply of DC current, a third electrode 50 is provided. The orifice 17 and the cylindrical projection 20 are otherwise as described in FIG. 2. Operation of this embodiment is similar to that described with respect to FIG. 1, except that DC current is applied to two of the electrodes 23, 24 whereas the voltage, or changes in voltage, are measured by one of the two current electrodes 23 and the third electrode 50, thus providing improved signal-to-noise ratios.

The embodiment FIG. 5 is again similar except that in addition to the electrodes 23, 24 used for supply of DC current, a third and fourth electrodes 50, 51 are provided. The voltage and voltage changes are measured by these additional electrodes 50, 51.

Figure 6:
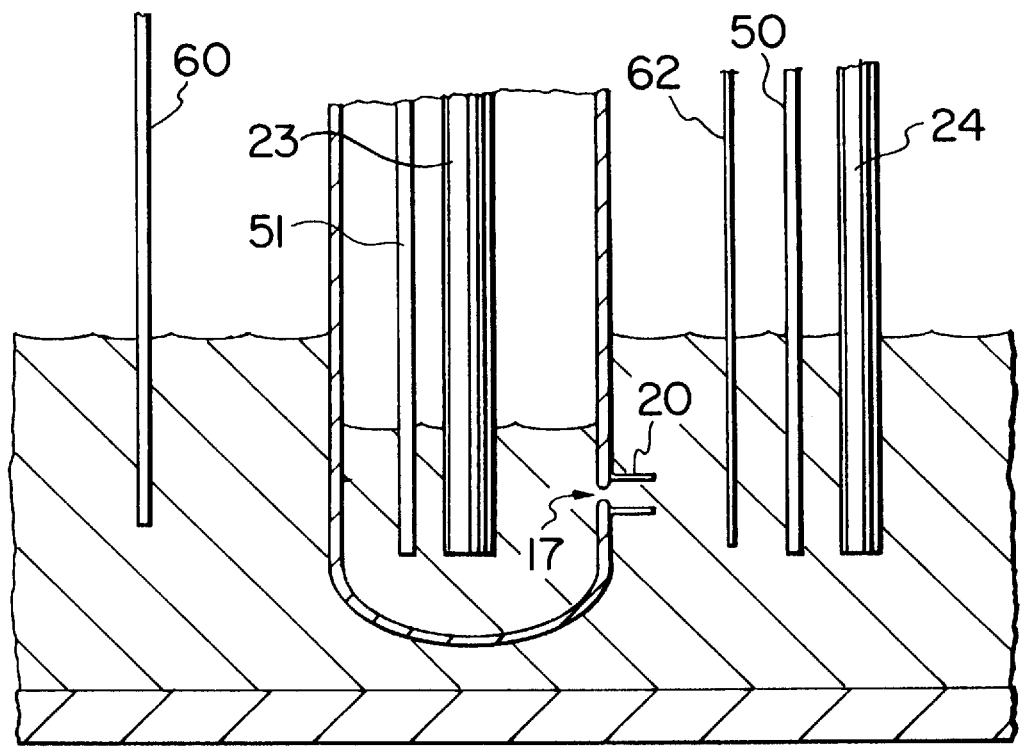

The embodiment FIG. 6 is similar to FIG. 5 except that a fifth and sixth electrodes 60, 61 are provided. One of these electrodes may be used in combination with electrode 51 to measure changes in the orifice diameter, and the other is used as a ground for the measurement electronics. These are more fully described in U.S. Pat. No. 5,130,639.

Figure 7:
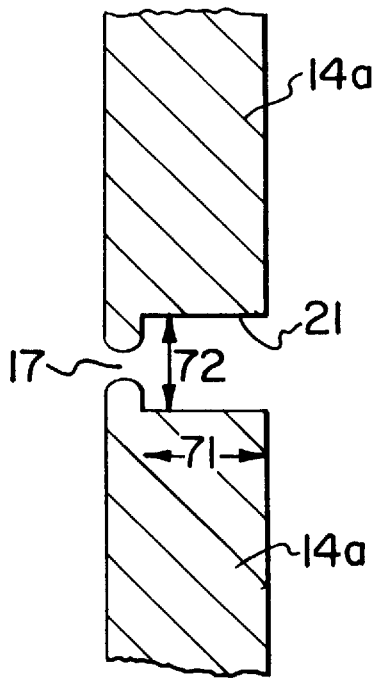
FIG. 7 is an enlarged cross-section similar to FIG. 2 showing a third embodiment of an orifice and passage.

FIG. 7 shows a detail of yet another embodiment of the invention. In this embodiment, the orifice 17 and a cylindrical passage 21 are formed in the wall 14a of the test vessel. The wall is made of material which is thicker than normal (at least in the area of the orifice) to permit this. The passage 21 has a portion of length 71 which has constant diameter 72. The ratio of the diameter 72 to the orifice diameter lies between 2 and 10, and the ratio of length 71 to diameter 72 is preferably at least 1. The ratio of the length 71 to the square of diameter 72 is more preferably at least 1000 meters$^{-1}$.

Although not wishing to be bound by any theory, it is believed that the invention operates by the balancing of several forces within the passage defined by the tubular projection (or its equivalent) in a unique manner. Molten metal containing inclusions is normally confined to a trough or similar vessel for measurement of the particle concentrations and flows through it. The flow is usually turbulent and therefore all inclusions, whether solid, liquid or gaseous, are kept in suspension. It is believed that provision of a passage 21 in advance of the measurement orifice 17 provides a region where the metal, moving only under the forces of the vacuum within the vessel 14, flows in a laminar manner, and thereby reduces or removes the effect of turbulent mixing on particle motion. Although gravitational forces can therefore cause particles to separate in such a stream depending on their density if a passage of sufficient diameter and length is provided to ensure an adequate residence time, such a separation is not reliable because density differences are small(except possibly for gases) and particles of the same type may have different densities which impact on the separation process. For example, large solid particles (which are important to measure) may settle out of the stream and fail to pass through the measurement orifice.

The present invention (which applies specific limits to the hydrodynamic diameter of the passage) overcomes such shortcomings, by using hydrodynamic drag forces balanced with magnetohydrodynamic forces in a unique and unexpected manner as explained below to ensure proper separation of the undesirable liquid and gaseous particles from the solid particles.

The passage 21 is of relatively small diameter, less than or equal to 10 times the diameter of the orifice itself, and in operation has a high current density with resulting high magnetohydrodynamic forces acting on any non-conductive particles. The force $F_{MHD}$ is given (in SI units) by the equation:

$$F_{MHD} = \frac{2\mu_0 I^2 d_p^3 R}{\pi D^4}$$

wherein: I is the current between the electrodes
$d_p$ is the diameter of the particle
R is the radial distance from the centre of the passage
D is the diameter of the passage
$\mu_0$ is the permittivity constant($4\pi \times 10^{-7}$ in SI units)

For a typical case of a 40 micrometer particle and a current of 60 amperes and a 1 mm diameter cylindrical tube, the maximum force is $9.2 \times 10^{-8}$ Newtons (approximately 122 times the gravitational force acting on the particle). This causes all such particles (solid, liquid or gaseous), regardless of density, to move at right angles to the current flow (that is towards the walls of the passage 21), opposed by the forces created by the metal viscosity, at a velocity $v_s$ defined by these forces. The force has a strong dependency on passage diameter, and if too large a diameter passage is used, the force rapidly diminishes to an ineffective level. As the current is in practical cases determined by the orifice size (as described in U.S. Pat. No. 4,555,662), the limitation on passage size in terms of the ratio of its hydrodynamic diameter to orifice diameter is clear.

Provided a passage of suitable length is available, substantially all particles can reach the wall. Integrating the velocity $v_s$ between radii representing the annular section of the passage containing the fraction of particles (preferably at least 90% and most preferably 95%) which are to reach the wall, the residence time in the passage, and hence the required length of the passage for any particular metal flow velocity within the tube can be determined. For at least one common situation, that of a particle having a particle Reynolds number of less than unity, this length is found to be proportional to the square of the passage diameter.

For example, a cylindrical passage of about 1 mm in diameter can remove substantially all particles of size greater than 20 micrometers to the walls in a length of less than 10 mm (preferably 3 to 6 mm) in aluminum (depending on the criteria for "complete removal") when a metal flowrate of 16 cm$^3$/min and a current of 60 amps are provided. These are typical operating parameters for a test vessel with an orifice diameter of 0.3 mm. The ratio of length to the square of the diameter lies within the preferred range of the ratio of the length to square of diameters and represents a practical size for construction in commonly available materials.

Under the effect of the magnetohydrbdynamic forces, all non-conductive particles will be carried to the wall, with an effectiveness only dependent on their size and not on their densities. It is believed that at the wall, the magnetohydrodynamic forces are sufficiently large that gaseous and liquid particles become flattened and attach firmly to the walls. Solid particles, however, are not attached in this manner, and the drag forces of the metal flowing through the passage of relatively small cross-section (i.e. defined by the limits on passage hydrodynamic diameter) are sufficient to carry them on and through the orifice, where they are measured. Thus the surprising separation of solid from gaseous and liquid particles occurs, and moreover the measurement of solid particles is not affected by the substantial magnetohydrodynamic forces acting within the passage. The combined effects of the magnetohydrodynamic and drag forces are most effective if the former is perpendicular to the axis of the passage and the latter is parallel to the axis. Where the passage is constant in cross-section, this is believed to be most likely to occur, and thus having at least a portion of the length of the passage of constant cross-section is advantageous. Preferably most of the passage is of constant cross-section, since this is generally easiest to fabricate.

If this additional effect of metal flow were not present, it would be possible to use very low metal flows and very short passage length to diameter ratios to force substantially all particles to the walls, but as there is a minimum velocity required to ensure that the drag forces caused by the metal flow will carry along the solid particles, this means that a passage length at least equal to the passage diameter is desirable, or more preferably a ratio of length to square of diameter of at least 1000 m$^{-1}$ is required.

The passage must not alter the measurement function significantly. This means that the passage of a particle through the passage must not cause a significant change in voltage and thereby affect the voltage signal response to particle passage. This would occur if the passage hydrodynamic diameter is too small, and therefore the passage hydrodynamic diameter should most preferably be at least two times the hydrodynamic diameter of the orifice. There is no upper limit on the length of the passage since this affects only the DC voltage measurement, but various practical construction considerations would limit such a length. For example, there is no need for a passage length to exceed 5 to 10 times the preferred minimum lengths, although longer passages can operate effectively.

While the invention has been described in detail above, it will be apparent to persons skilled in the art that various modifications and alterations may be made without departing from the spirit and scope of the invention. All such modifications and alterations form part of this invention.

What I claim is:

1. A method of separatly detecting and measuring solid particles suspended in a molten metal in the presence of liquid or gaseous particles, comprising:

moving molten metal through an orifice of predetermined hydrodynamic diameter provided in an electrically non-conductive barrier, as the molten metal is moved through the orifice, establishing a current path passing through the orifice from electrodes positioned on opposite sides of said barrier, detecting changes in voltage of said current as the metal is moved through the orifice, and determining the presence and size of said solid particles suspended in said metal moved through said orifice from said voltage changes;

wherein said metal, immediately before being moved through said orifice, is moved through a passage positioned in said current path defined by an electrically non-conductive surface, said passage including a region having a hydrodynamic diameter of between 2 and 10 times said hydrodynamic diameter of the orifice, at least a part of said region being of substantially constant hydrodynamic diameter.

2. A method according to claim 1, wherein said orifice is circular and said passage is of circular cross section at least within said part of substantially constant hydrodynamic diameter.

3. A method according to claim 1, wherein said region has a length that is at least equal to said hydrodynamic diameter of the passage.

4. A method according to claim 1, wherein a ratio of the length of the said region to a square of the said hydrodynamic diameter of the part of the passage of substantially constant hydrodynamic diameter is at least 1000 meters$^{-1}$.

5. A method according to claim 1, wherein said passage has said part of substantially constant hydrodynamic diameter adjacent to an outer end of the passage remote from said orifice, and said passage has a second part of smaller hydrodynamic diameter than the diameter of said part of substantially constant diameter, adjacent to the orifice.

6. A method according to claim 5, wherein said second part of the passage has a hydrodynamic diameter that reduces in size from one end adjacent to said part of the passage of substantially constant diameter to an opposite end adjacent to said orifice.

7. Apparatus for separately detecting and measuring suspended solid particles in a molten metal in the presence of liquid or gaseous particles, comprising;

an electrically non-conductive barrier having opposed sides and having an orifice of predetermined hydrodynamic diameter, said barrier being suitable for immersion in a molten metal with said orifice below a surface of the metal;

a device for moving molten metal through the orifice in a direction from one side of the barrier to the other;

electrodes, suitable for immersion in said molten metal, positioned on opposite sides of said barrier for establishing a current path in the molten metal passing through said orifice;

a current generator connectable to said electrodes when said barrier and said electrodes are immersed in said molten metal;

a voltage detecting device for detecting changes in voltage as current flows through said molten metal between said electrodes as said molten metal moves through said orifice; and processing apparatus for detecting and determining the number of solid particles in molten metal passing through the orifice from said changes in voltage;

said apparatus including an electrically non-conductive surface adjacent to an upstream side of said orifice, considered in said direction of movement of said metal through the orifice, defining a passage for conveying molten metal to said orifice, said passage including a region having a hydrodynamic diameter of between 2 and 10 times said hydrodynamic diameter of the orifice, at least a part of said region being of substantially constant hydrodynamic diameter.

8. Apparatus according to claim 7, wherein said orifice is circular and said passage has a circular internal cross-section, at least within said part of substantially constant cross-section.

9. Apparatus according to claim 7, wherein said region has a length that is at least equal to the said hydrodynamic diameter of the passage in said part of substantially constant hydrodynamic diameter.

10. Apparatus according to claim 7, wherein a ratio of the length of said region to a square of said hydrodynamic diameter of the part of substantially constant hydrodynamic diameter is at least 1000 meters$^{-1}$.

11. Apparatus according to claim 7, wherein said part of said passage of substantially constant hydrodynamic diameter is located at an end of said passage remote from said orifice, and said passage has a second part, positioned between said part of substantially constant hydrodynamic diameter and said orifice, of smaller hydrodynamic diameter than said part of substantially constant hydrodynamic diameter.

12. Apparatus according to claim 11, wherein the hydrodynamic diameter of the second part reduces in size in a direction approaching the orifice.

13. Apparatus according to claim 7, wherein the said passage is of circular cross-section, at least in said part of substantially constant hydrodynamic diameter.

14. A probe for use as part of apparatus for separately detecting and measuring suspended solid particles in a molten metal in the presence of liquid or gaseous particles, said probe comprising:

an electrically non-conductive barrier resistant to damage by molten metal and provided with an orifice of predetermined hydrodynamic diameter; and an electrically non-conductive surface adjacent to an upstream side of said orifice, considered in said direction of movement of said molten metal through the orifice, defining a passage for conveying molten metal to said orifice, said passage including a region having a hydrodynamic diameter of between 2 and 10 times said hydrodynamic diameter of the orifice, at least a part of said region being of substantially constant hydrodynamic diameter.

15. A probe according to claim 14 wherein said barrier forms an outer wall of a test vessel having an interior that can be evacuated.

16. A probe for use as part of apparatus for detecting and measuring suspended solid particles in a molten metal containing in the presence of liquid or gaseous particles, said probe comprising:

an electrically non-conductive barrier forming an outer wall of a test vessel having an interior that can be evacuated, said barrier being resistant to damage by molten metal and provided with an orifice of predetermined hydrodynamic diameter; and an electrically non-conductive surface adjacent to an upstream side of said orifice, considered in said direction of movement of said metal through the orifice, defining a passage for conveying molten metal to said orifice, said passage including a region having a hydrodynamic diameter of between 2 and 10 times said hydrodynamic diameter, of the orifice, at least a part of said region being of substantially constant hydrodyamic diameter;

wherein said surface is an internal surface of a tubular projection extending outwardly from said test vessel and surrounding said orifice.

17. A probe according to claim 14, wherein said orifice is circular and said passage has a circular cross-section.

18. A probe according to claim 14, wherein said region has a length at least equal to the said hydrodynamic diameter of said part of substantially constant cross-section.

19. A probe according to claim 14, wherein a ratio of the length of said region to a square of the said hydrodynamic diameter of said passage within said part of substantially constant cross-section is at least 1000 meters$^{-1}$.

20. A probe according to claim 14, wherein said part of said passage of substantially constant hydrodynamic diameter is at an end of said passage remote from said orifice, and said passage has a second part, adjacent to said orifice, of smaller hydrodynamic diameter than the hydrodynamic diameter of the part of the passage of substantially constant hydrodynamic diameter.

21. A probe according to claim 20, wherein said second part has a hydrodynamic diameter that reduces in size in a direction approaching the orifice.

22. A probe according to claim 14, wherein the said passage is circular in cross section.

23. A method of detecting and measuring solid particles suspended in a molten metal, comprising:

moving molten metal through an orifice of predetermined hydrodynamic diameter provided in an electrically non-conductive barrier, as the molten metal is moved through the orifice, establishing a current path passing through the orifice from electrodes positioned on opposite sides of said barrier, detecting changes in voltage of said current as the metal is moved through the orifice, and determining the presence and size of particles suspended in said metal moved through said orifice from said voltage changes;

wherein said metal, immediately before being moved through said orifice, is moved through a passage positioned in said current path defined by an electrically non-conductive hollow open-ended projection from said barrier, said passage including a region having a hydrodynamic diameter of between 2 and 10 times said hydrodynamic diameter of the orifice.

24. Apparatus for detecting and measuring suspended solid particles in a molten metal, comprising:

an electrically non-conductive barrier having opposed sides and having an orifice of predetermined hydrodynamic diameter, said barrier being suitable for immersion in a molten metal with said orifice below a surface of the metal;

a device for moving molten metal through the orifice in a direction from one side of the barrier to the other;

electrodes, suitable for immersion in said metal, positioned on opposite sides of said barrier for establishing a current path in the metal passing through said orifice;

a current generator connectable to said electrodes when said barrier and said electrodes are immersed in said metal;

a voltage detecting device for detecting changes in voltage as current flows through said metal between said electrodes as said metal moves through said orifice; and processing apparatus for detecting and determining the number of particles in molten metal passing through the orifice from said changes in voltage;

said apparatus including an electrically non-conductive hollow open-ended projection adjacent to an upstream side of said orifice, considered in said direction of movement of said metal through the orifice, defining a passage for conveying molten metal to said orifice, said passage including a region having a hydrodynamic diameter of between 2 and 10 times said hydrodynamic diameter of the orifice.

25. A probe for use as part of apparatus for detecting and measuring suspended solid particles in a molten metal, said probe comprising:

an electrically non-conductive barrier resistant to damage by molten metal and provided with an orifice of predetermined hydrodynamic diameter; and an electrically non-conductive hollow open-ended projection adjacent to an upstream side of said orifice, considered in said direction of movement of said metal through the orifice, defining a passage for conveying molten metal to said orifice, said passage including a region having a hydrodynamic diameter of between 2 and 10 times said hydrodynamic diameter of the orifice.

26. A probe according to claim 16, wherein said orifice is circular and said passage has a circular internal cross-section, at least within said part of substantially constant cross-section.

27. A probe according to claim 16, wherein said region has a length that is at least equal to the said hydrodynamic diameter of the passage in said part of substantially constant hydrodynamic diameter.

28. A probe according to claim 16, wherein a ratio of the length of said region to a square of said hydrodynamic diameter of the part of substantially constant hydrodynamic diameter is at least 1000 meters$^{-1}$.

29. A probe according to claim 16, wherein said part of said region of substantially constant cross-section is located at an end of said passage remote from said orifice, and said passage has a second part, positioned between said part of substantially constant hydrodynamic diameter and said orifice, of smaller hydrodynamic diameter than said part of substantially constant hydrodynamic diameter.

30. A probe according to claim 29, wherein the hydrodynamic diameter of the second part reduces in size in a direction approaching the orifice.

31. A probe according to claim 16, wherein the said passage is of circular cross-section, at least in said part of substantially constant hydrodynamic diameter.

32. A method according to claim 23, wherein at least part of said region is of substantially constant hydrodynamic diameter.

33. A method according to claim 32, wherein said orifice is circular and said passage has a circular internal cross-section, at least within said part of substantially constant cross-section.

34. A method according to claim 32, wherein said region has a length that is at least equal to the said hydrodynamic diameter of the passage in said part of substantially constant hydrodynamic diameter.

35. A method according to claim 32, wherein a ratio of the length of said region to a square of said hydrodynamic diameter of the part of substantially constant hydrodynamic diameter is at least 1000 meters$^{-1}$.

36. A method according to claim 32, wherein said part of said passage of substantially constant cross-section is located at an end of said passage remote from said orifice, and said passage has a second part, positioned between said part of substantially constant hydrodynamic diameter and said orifice, of smaller hydrodynamic diameter than said part of substantially constant hydrodynamic diameter.

37. A method according to claim 36, wherein the hydrodynamic diameter of the second part reduces in size in a direction approaching the orifice.

38. A method according to claim 32, wherein the said passage is of circular cross-section, at least in said part of substantially constant hydrodynamic diameter.

39. Apparatus according to claim 24, wherein at least part of said region is of substantially constant hydrodynamic diameter.

40. Apparatus according to claim 24, wherein said orifice is circular and said passage has a circular internal cross-section, at least within said part of substantially constant cross-section.

41. Apparatus according to claim 39, wherein said region has a length that is at least equal to the said hydrodynamic diameter of the passage in said part of substantially constant hydrodynamic diameter.

42. Apparatus according to claim 39, wherein a ratio of the length of said region to a square of said hydrodynamic diameter of the part of substantially constant hydrodynamic diameter is at least 1000 meters$^{-1}$.

43. Apparatus according to claim 39, wherein said part of said passage of substantially constant cross-section is located at an end of said passage remote from said orifice, and said passage has a second part, positioned between said part of substantially constant hydrodynamic diameter and said orifice, of smaller hydrodynamic diameter than said part of substantially constant hydrodynamic diameter.

44. Apparatus according to claim 43, wherein the hydrodynamic diameter of the second part reduces in size in a direction approaching the orifice.

45. Apparatus according to claim 39, wherein the said passage is of circular cross-section, at least in said part of substantially constant hydrodynamic diameter.

46. A probe according to claim 25, wherein at least part of said region is of substantially constant hydrodynamic diameter.

47. A probe according to claim 46, wherein said orifice is circular and said passage has a circular internal cross-section, at least within said part of substantially constant cross-section.

48. A probe according to claim 46, wherein said region has a length that is at least equal to the said hydrodynamic diameter of the passage in said part of substantially constant hydrodynamic diameter.

49. A probe according to claim 46, wherein a ratio of the length of said region to a square of said hydrodynamic diameter of the part of substantially constant hydrodynamic diameter is at least 1000 meters$^{-1}$.

50. A probe according to claim 46, wherein said part of said passage of substantially constant cross-section is located at an end of said passage remote from said orifice, and said passage has a second part, positioned between said part of substantially constant hydrodynamic diameter and said orifice, of smaller hydrodynamic diameter than said part of substantially constant hydrodynamic diameter.

51. A probe according to claim 50, wherein the hydrodynamic diameter of the second part reduces in size in a direction approaching the orifice.

52. A probe according to claim 46, wherein the said passage is of circular cross-section, at least in said part of substantially constant hydrodynamic diameter.

* * * * *